United States Patent [19]

Terry et al.

[11] Patent Number: 4,957,948
[45] Date of Patent: Sep. 18, 1990

[54] BIOCIDAL PROTECTIVE COATING FOR HEAT EXCHANGER COILS

[75] Inventors: Claude E. Terry, Kennesaw, Ga.; Robert H. McIntosh, Sr., Greensboro, N.C.

[73] Assignee: Interface, Inc., Atlanta, Ga.

[21] Appl. No.: 242,484

[22] Filed: Sep. 9, 1988

Related U.S. Application Data

[63] Continuation-in-part of Ser. No. 190,370, May 5, 1988, Pat. No. 4,908,209, which is a continuation-in-part of Ser. No. 47,561, Apr. 27, 1987, which is a continuation-in-part of Ser. No. 781,710, Oct. 2, 1985, which is a continuation-in-part of Ser. No. 635,728, Oct. 9, 1984, abandoned, which is a continuation-in-part of Ser. No. 713,445, Mar. 19, 1985, abandoned, which is a continuation-in-part of Ser. No. 736,652, May 21, 1985, Pat. No. 4,647,601, which is a continuation-in-part of Ser. No. 744,730, Jun. 13, 1985, abandoned, which is a continuation-in-part of Ser. No. 570,952, Mar. 8, 1984, Pat. No. 4,608,289, which is a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned.

[51] Int. Cl.$^5$ .......................... B05D 1/18; B05D 3/02
[52] U.S. Cl. .............................. 523/122; 427/388.1; 427/388.5; 427/421; 427/429; 427/435
[58] Field of Search ............... 424/405; 514/76, 107; 427/388.1, 388.5, 421, 429, 435; 523/122

[56] References Cited

U.S. PATENT DOCUMENTS

| | | | |
|---|---|---|---|
| 2,202,124 | 5/1940 | Tattersal | 106/18.17 |
| 2,272,668 | 2/1942 | Honel | 558/113 |
| 2,337,424 | 12/1943 | Stoner et al. | 260/86 |
| 2,541,088 | 2/1951 | Nikawitz | 260/584 |
| 2,552,325 | 5/1951 | Kosolapoff | 260/461 |
| 2,592,564 | 4/1952 | Hardman | 106/273 |
| 2,676,122 | 4/1954 | McCarthy | 117/139.5 |
| 2,756,175 | 7/1956 | Goldstein et al. | 167/33 |
| 2,831,782 | 4/1958 | Zvanut | 117/127 |
| 2,872,351 | 2/1959 | Wedell | 117/121 |
| 2,891,878 | 6/1959 | Chamberlain | 428/421 |
| 2,922,738 | 1/1960 | McDermott et al. | 167/22 |
| 2,935,490 | 5/1960 | Havens et al. | 260/45.7 |
| 2,960,529 | 11/1960 | McCall et al. | 260/461 |
| 2,970,081 | 1/1961 | McCall et al. | 167/30 |
| 2,976,186 | 3/1961 | Thompson et al. | 260/45.8 |
| 2,997,454 | 8/1961 | Leistner et al. | 260/458 |
| 3,247,134 | 4/1966 | Hwa et al. | 260/2.5 |
| 3,279,986 | 10/1966 | Hyman | 167/42 |
| 3,280,131 | 10/1966 | Wakeman et al. | 260/286 |
| 3,294,775 | 12/1966 | Wasserman | 260/100 |
| 3,308,488 | 3/1967 | Schoonman | 5/355 |
| 3,312,623 | 4/1967 | Fitch et al. | 252/106 |
| 3,364,192 | 1/1968 | Leach | 260/94.9 |
| 3,404,140 | 10/1968 | Fukumoto et al. | 260/93.7 |
| 3,428,713 | 2/1969 | Bartlett et al. | 260/924 |
| 3,437,473 | 4/1969 | Driscoll | 514/107 X |
| 3,475,204 | 10/1969 | Patterson | 147/138.8 |
| 3,498,969 | 3/1970 | Lewis | 260/211 |
| 3,527,726 | 9/1970 | Gower et al. | 260/29.6 |
| 3,577,515 | 5/1971 | Vandegaer | 424/32 |

(List continued on next page.)

FOREIGN PATENT DOCUMENTS

| | | |
|---|---|---|
| 1162356 | 2/1984 | Canada . |
| 80101498.6 | 3/1980 | European Pat. Off. . |
| 0035375 | 9/1981 | European Pat. Off. . |
| 1228031 | 11/1966 | Fed. Rep. of Germany . |
| 2530584 | 1/1977 | Fed. Rep. of Germany . |
| 3014765 | 10/1981 | Fed. Rep. of Germany . |
| 3248708.8 | 12/1982 | Fed. Rep. of Germany . |
| 2157952A | 11/1985 | Fed. Rep. of Germany . |
| 53-081577 | 7/1978 | Japan . |
| 617854 | 6/1980 | Switzerland . |
| 3039437 | 5/1982 | Switzerland . |
| 1122664 | 11/1984 | U.S.S.R. . |
| 1036578 | 7/1966 | United Kingdom . |
| 1302894 | 1/1973 | United Kingdom . |
| 2042574 | 9/1983 | United Kingdom . |
| 2131029 | 1/1986 | United Kingdom . |

OTHER PUBLICATIONS

Yuan et al., *Phosphorus and Sulphur*, vol. 18, 323-326 (1983).
Nakamura, *Journal of Radioanalytical Chemistry*, 52 (2) 343-354 (1979).
Nakamura, *Journal of Radioanalytical Chemistry*, 44 37-47 (1978).
Partridtge et al., *J. Inorg. Nucl. Chem.*, 31 2587-2589 (1969).
Tachimori et al., *Journal of Radioanalytical Chemistry*, 67 (2) 329-337 (1981).
Honaker et al., *J. Inorg. Nucl. Chem.*, 39 1703-1704 (1977).
J. Perka et al., *Tenside Detergents* 15 295-298 (1978)6.
Sorbe et al., *Quim. Apl. Jorn. Com. Esp. Deterg.* 11th 415-430 (1980).
Yoshihira Koda et al., "The Synthesis of Surfactant and the Use Thereof", pp. 96-99 and 436-477 (1977).

(List continued on next page.)

*Primary Examiner*—Thurman K. Page
*Attorney, Agent, or Firm*—Kilpatrick & Cody

[57] ABSTRACT

An biocidal protective coating and an method for coating heat exchanger coils, which includes a polymeric composition comprising an organic water resistant polymer and a compound of the general formula

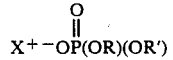

wherein X is selected from the group consisting of organic ions, H$^T$, Group I metals, Group II metals and transition metals, R and R' are independently selected from the group consisting of hydrocarbons and substituted hydrocarbons of not more than 24 carbon atoms, and there is at least one free hydroxyl group.

33 Claims, No Drawings

U.S. PATENT DOCUMENTS

| | | | |
|---|---|---|---|
| 3,620,453 | 11/1971 | Gancbeg et al. | 239/60 |
| 3,639,594 | 2/1972 | Notarianni et al. | 424/224 |
| 3,641,226 | 2/1972 | Partridge et al. | 260/990 |
| 3,671,304 | 6/1972 | Mischutin | 117/138 |
| 3,697,655 | 10/1972 | Berenson et al. | 514/107 |
| 3,705,235 | 12/1972 | McIntosh et al. | 424/83 |
| 3,708,573 | 1/1973 | Yoshinaga et al. | 260/29.6 |
| 3,714,256 | 1/1973 | Samour et al. | 260/29.6 |
| 3,758,283 | 9/1973 | Matt | 44/62 |
| 3,762,415 | 10/1973 | Morrison | 128/290 |
| 3,769,377 | 10/1973 | DeSelms | 260/958 |
| 3,776,806 | 12/1973 | Mayer et al. | 161/88 |
| 3,819,656 | 6/1974 | Barie, Jr. et al. | 260/343.7 |
| 3,873,648 | 3/1975 | Balde | 260/990 |
| 3,885,000 | 5/1975 | Beriger et al. | 260/956 |
| 3,888,978 | 6/1975 | Düwel et al. | 514/76 |
| 3,896,101 | 7/1975 | McIntosh et al. | 260/93.7 |
| 3,897,491 | 7/1975 | Toy et al. | 260/543 P |
| 3,897,521 | 7/1975 | Beriger et al. | 260/948 |
| 3,919,410 | 11/1975 | McIntosh et al. | 424/78 |
| 3,920,836 | 11/1975 | McIntosh et al. | 424/315 |
| 3,925,442 | 12/1975 | Samour | 424/315 |
| 3,928,563 | 12/1975 | McIntosh et al. | 424/78 |
| 3,932,612 | 1/1976 | Burkhardt et al. | 424/78 |
| 3,933,947 | 1/1976 | Kishino et al. | 260/949 |
| 3,959,556 | 5/1976 | Morrison | 428/364 |
| 3,972,243 | 8/1976 | Driscoll et al. | 74/200 |
| 3,979,307 | 9/1976 | Kolaian et al. | 252/8.75 |
| 3,991,187 | 11/1976 | Hogberg et al. | 424/199 |
| 4,004,001 | 1/1977 | Large et al. | 424/200 |
| 4,006,204 | 2/1977 | Rajadhyaksha et al. | 260/958 |
| 4,024,324 | 5/1977 | Sparks | 526/2 |
| 4,025,583 | 5/1977 | Mead et al. | 260/925 |
| 4,039,636 | 8/1977 | Claus et al. | 260/963 |
| 4,071,552 | 1/1978 | Ferland et al. | 260/562 R |
| 4,083,860 | 4/1978 | Ruf | 260/403 |
| 4,094,970 | 6/1978 | Behrenz et al. | 424/78 |
| 4,107,292 | 8/1978 | Nemeth | 424/78 |
| 4,110,504 | 8/1978 | Hull et al. | 428/97 |
| 4,119,724 | 10/1978 | Thizy et al. | 424/45 |
| 4,139,616 | 2/1979 | Ducret et al. | 424/222 |
| 4,152,421 | 5/1979 | Tsutsumi et al. | 424/57 |
| 4,165,369 | 9/1979 | Watanabe et al. | 71/93 |
| 4,209,398 | 6/1980 | Ii et al. | 210/58 |
| 4,235,733 | 11/1980 | Watanabe et al. | 252/107 |
| 4,255,259 | 3/1981 | Hwa et al. | 210/699 |
| 4,259,078 | 3/1981 | Kleber et al. | 8/188 |
| 4,272,395 | 6/1981 | Wright | 424/70 |
| 4,276,418 | 6/1981 | Howarth | 544/243 |
| 4,289,634 | 9/1981 | Lewis et al. | 252/32.5 |
| 4,343,853 | 8/1982 | Morrison | 428/233 |
| 4,361,611 | 11/1982 | Schafer et al. | 428/96 |
| 4,363,663 | 12/1982 | Hill | 106/18.31 |
| 4,401,712 | 8/1983 | Morrison | 428/289 |
| 4,432,833 | 2/1984 | Breese | 162/138 |
| 4,442,095 | 4/1984 | Johnston | 544/120 |
| 4,442,096 | 4/1984 | Johnston | 424/250 |
| 4,560,599 | 12/1985 | Regen | 428/36 |
| 4,598,006 | 7/1986 | Sand | 424/81 |
| 4,647,601 | 3/1987 | McIntosh | 523/122 |
| 4,661,477 | 4/1987 | Privitzer et al. | 514/76 |
| 4,770,694 | 9/1988 | Iwasaki et al. | 252/106 |

OTHER PUBLICATIONS

Takehiko Fujimoto, "Introduction in New Surfactant", pp. 295–297 (1974), *J. Inorg. Nucl. Chem.*, 38 2127–2129 (1976).

Matsui et al., *Chem. Abstracts* 82, 141561 (1974) (JP 74 24,806).

Ogasawara et al., *Chem. Abstracts* 81, 107078f (1974) (U.S. Patent No. 3,799,904).

Hall et al., *Chem. Abstracts* 80, 123000 (1973) *ASLE Trans.* 16(4), 291–296.

Keil et al., *Chem. Abstracts* 76, 101944k (1972) Ger. Offen. 2,030,256.

Sudakova et al., *Chem. Abstracts* 70, 56711v (1969) (USSR 229,879).

Gialkdi et al., *Chem. Abstracts* 43, 6363a (1949) (*Farm. Sci. E Tec.* 4, 166–175.

Tak Chemicals Ltd. 1580026 (Jun. 1977).

McCoy, *Microbiology of Cooling Water*, 94–95 (Chemical Pub. Co., N.Y. 1980).

*Derivatives of Anhydro Acids*, 348.

BIOCIDAL PROTECTIVE COATING FOR HEAT EXCHANGER COILS

BACKGROUND OF THE INVENTION

This application is a continuation-in-part of U.S. Ser. No. 190,370 May 5, 1988 now U.S. Pat. No. 4,908,209, by Robert H. McIntosh et al entitled "Biocidal Delivery System and Method of Preparation Thereof" which is a continuation in part of U.S. Ser. No. 047,561, filed Apr. 27, 1987, entitled "Microbiocidal Composition and Method of Preparation Thereof" by Robert H. McIntosh, which is a continuation-in-part of U.S. Ser. No. 781,710, filed Oct. 2, 1985; U.S. Ser. No.; 635,728, filed Oct. 9, 1984, now abandoned; U.S. Ser. No. 713,445, filed Mar. 19, 1985, now abandoned; U.S. Ser. No. 736,652, filed May 21, 1985, now U.S. Pat. No. 4,647,601; U.S. Ser. No. 744,730, filed June 13, 1985, now abandoned; all of which are continuation-in-part of U.S. Ser. No. 570,952, filed Mar. 8, 1984 U.S. Pat. No. 4,608,289, a continuation of U.S. Ser. No. 523,734, filed Aug. 16, 1983, now abandoned, which is a continuation of U.S. Ser. No. 226,006, filed Jan. 19, 1981, now abandoned, which is a continuation of U.S. Ser. No. 930,879, filed Aug. 4, 1978, now abandoned.

This invention relates to a coating for, and method of coating, heat exchanging coils.

Heat exchangers are typically metal coils which conduct heat from one fluid to another fluid, such as from water or Freon (chlorofluorocarbon) inside the coils to air surrounding the coils. Examples of such coils are found in air conditioners, heaters, refrigerators and dehumidifiers. These coils are usually manufactured from a metal such as copper, iron, brass, or aluminum, or from a metal alloy which contains zinc, manganese, silicon, chromium, nickel, magnesium or carbon. Metals are the preferred materials for heat exchangers because of their high heat transfer coefficient. Aluminum heat exchangers are widely used for car air conditioners because of their light weight, and the fact that aluminum is more efficient than steel as a heat exchange material.

Although metal heat exchanger coils are preferred for their heat transmission properties, they develop at least three very damaging conditions over time with use and exposure to the environment. First, the exterior surface of metal coils corrode on exposure to moisture and other airborne chemicals. Moisture in the air condenses on cooling coils, causing a buildup of water on the surface. The moisture corrodes the coils, causing them to be etched and pitted. This reduces the strength of the coil, and shortens the useful life and efficiency of the unit. This is especially true in areas which have a high salt content in the air.

Second, heat exchanging metal coils experience "fouling," which is the accumulation of dust and other particulate matter on the surface. Fouling decreases the efficiency of heat transfer because the particulate matter lining the outer surface of the coil generally has low thermal conductivity. In addition, fouling contributes a bad odor to the surroundings.

Perhaps the most important problem associated with the use of metal heat exchanging coils is the buildup of bacterial and fungal growth on the surface of the coils. These organisms tend to accumulate and propagate on the surface because of the presence of the moisture and particulate matter. In particular, fungi such as *Aspergillus niger, Aspergillus flavus*, and *Pencillin funiculogum*, and bacteria such as *Staphylococcus aureus* (Gram-positive) and *Pseudomonas aeroginosa* (Gram-negative) are known to grow under these conditions. These organisms produce a foul odor in the environment and exacerbate allergy problems. In addition, the organisms have a low thermal conductivity, which decreases the efficiency of heat transfer.

Bacterial and fungal growth are an especially significant problem for automobile air conditioners and heating units. For example, when a car air conditioner is turned on, a fan forces air past the surface of the heat exchanger coils, blowing the particulate and bacterial buildup into the passenger area. Often a strong, foul musty odor is detected. Not only is the smell unpleasant, but it is unhealthy as well. The debris and organisms cause allergic reactions such as swollen, teary eyes, runny noses, sore throats and asthmatic reaction.

Likewise, in refrigerators and freezers, a fan forces air past cooling coils and into the food compartments. The cooled air carries organisms which may contaminate the food. Furthermore, when the cooling is stopped, for example, when the refrigerator is unplugged, the organisms, especially mold, proliferate.

It is clear that the three above-described problems associated with the use of metal heat exchanger coils, corrosion, fouling, and biocidal buildup, exacerbate each other. Fouling buildup occurs more rapidly when there is corrosion on the coils, and organisms proliferate at a faster rate when there is fouling particulate and moisture to feed on.

There is therefore a strong, long felt need to develop a coating for metal heat exchangers which reduces the corrosion, fouling and biocidal buildup on the exterior surface of the coils. A desirable such coating must be durable, efficient, and capable of being applied to coils during manufacture.

Therefore, it is an object of the present invention to provide a coating for heat exchanger coils which protects the exterior surface of the coils from corrosion caused by moisture and other chemicals.

It is another object of the present invention to provide a coating for heat exchanger coils which prevents the buildup of dust and particulate matter on the surface of the coil.

It is a further object of the present invention to provide a coating for heat exchanger coils which prevents the buildup of organisms on the surface of the coil.

It is still another object of the present invention to provide a coating for heat exchanger coils which is suitable for manufacturing scale.

It is a still further object of the present invention to provide a process to apply a biocidal protective coating to heat exchanger coils which is simple and efficient.

SUMMARY OF THE INVENTION

The present invention is a biocidal protective coating for heat exchanger coils and a method for applying such a coating. According to the present invention, coils are coated with a polymeric composition which includes an organic water resistant polymer which has associated with it a compound of the general formula

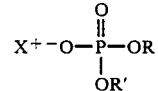

wherein R and R' are independently selected from the group consisting of hydrocarbons and substituted hydrocarbons, one of R or R' can be hydrogen, X is H+ a Group I metal ion, Group II metal ion, transition metal ion, or an organic ion such as a substituted ammonium ion, and there is at least one free hydroxyl group. In the present invention, the polymers or copolymers may be prepared from alkenes, dienes, vinyl esters, acrylics, methacrylates, vinyl halides, styrene, or vinylidene halides. It is preferred that at least some of the hydrogens on the polymer be replaced with fluorine.

The polymeric composition may also contain extenders or fillers such as clay, calcium carbonate, diatomatous earth, alumina trihydrate, barium sulphate, talc, calcium silicate or magnesium silicate, in a range of 0.5% to 10.0% by weight.

This polymeric composition is applied to the heat exchanger coils, in a thickness range of 0.5 mils to 5.0 mils, by dipping the coils into a dispersion of the polymeric composition, spraying the polymeric composition onto the coils, or brushing the polymeric composition onto the coils. The coils are then dried with or without heat.

This coating provides superior corrosion resistance, and minimizes fouling caused by the accumulation of dust and other particulate matter on the coil. In addition, the coating provides long-term biocidal activity against fungi and bacteria.

DETAILED DESCRIPTION OF THE INVENTION

The present invention is a biocidal protective coating for, and a method for coating, heat exchanger coils. According to the present invention, the coils are coated with a polymeric composition comprising an organic water resistant polymer which has associated with it a compound of the general formula

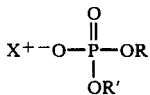

wherein R and R' are independently selected from the group consisting of hydrocarbons and substituted hydrocarbons, one of R or R' can be hydrogen, X is H+, a Group I metal ion, Group II metal ion, transition metal ion, or an organic ion such as a substituted ammonium ion, and there is at least one free hydroxyl group.

In particular, in the present invention, polymers or co-polymers made from alkenes, dienes, vinyl esters, vinyl ethers, acrylic acid, acrolein, alkyl methacrylate, methacrylic acid, acrylonitrile, vinyl halides and mixtures thereof, styrene, or vinylidene halide may be used.

Examples of such monomers include ethylene, propylene, butene, 2-methyl-2-propene, pentene, 3-methyl-1-butene, 1,3-butadiene, 1,3-pentadiene, 2-methyl-1,3-butadiene, 2,3-dimethyl-1,3-butadiene, chloroprene, vinyl acetate, vinyl propionate, vinyl butyrate, methoxyethylene, ethoxyethylene, propoxyethylene, acrylic acid, acrylonitrile, methyl methacrylate, ethyl methacrylate, propyl methacrylate, butyl methacrylate, isobutyl methacrylate, vinyl chloride, polytetrafluoroethylene, polychlorotrifluoroethylene, vinyl bromide, vinyl fluoride, vinylidene chloride, vinylidene bromide and vinylidene fluoride. It is preferred that at least some of the hydrogens of these monomers be replaced with halogens, preferably flourine, to increase the corrosion resistant properties of the coating. Chlorine or bromine may also be used. Contemplated equivalents include any monomers which when polymerized and associated with an alkyl phosphoric acid as described in the present invention, provides a water resistant biocidal protective coating.

Fluoropolymers can typically withstand exposure to a wide variety of chemical environments and some are useful at temperatures ranging from $-200°$ C. to as high as $260°$ C. Most fluoropolymers are totally insoluble in organic solvents and some are unaffected by strong acids or bases. In addition, they will not support combustion.

An example of a suitable polymeric material for use in this invention is Teflon ® NPA Soil and Stain Repellent, which is a proprietary composition of fluorochemicals and nonfluorochemicals made by E. I. DuPont NeMours and Co., which includes polyfunctional perfluoroalkyl esters and perfluoroalkylmethacrylate co-polymers.

Perfluorinated polymers may be used alone or in association with nonfluorinated polymers. Alternatively, different perfluorinated polymers may be used together. Nonfluorinated polymers may also be used together or in association with fluorinated polymers. Furthermore, perfluorinated monomers may be polymerized with nonfluorinated monomers to produce a suitable polymer for the heat exchange coating.

According to the present invention, an alkyl phosphoric acid or it salt of the general formula

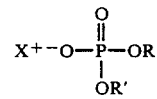

wherein R and R' are independently selected from the group consisting of hydrocarbons and substituted hydrocarbons, one of R or R' can be H, X is H+, a Group I metal ion, Group II metal ion, transition metal ion, or an organic ion such as an ammonium ion, is combined with the polymer to provide the coating with biocidal properties. Examples of hydrocarbon groups include alkyl, aryl, aralkyl and alkaryl groups including straight chains, branched chains or cyclic alkyl groups having from 2 to 24 carbon atoms, polyoxyethylene or polyoxypropylene having from 2 to 12 ethylene oxide or propylene oxide units respectively, alkyl phenoxy polyoxyethylene containing from 2 to 12 ethylene oxide units, alkyl phenoxy polyoxyethylene containing ethylene oxide units and from 2 to 24 carbon atoms in the phenolic alkyl chain, or a polyhydroxy compound such as ethylene glycol, glycerol, or sorbitol. Furthermore, these hydrocarbons may be substituted with organic groups or inorganic moieties such as Cl, Br, F and I. The biocidal properties of these compounds have been described in copending application, "Microbiocidal Composition and Method of Preparation Thereof", filed by Robert H. McIntosh, Jr. on Apr. 27, 1987, U.S. Ser. No. 047,561, incorporated herein by reference. The alkyl phosphoric acid or derivative thereof may be mixed in the polymeric composition in a range of up to 10%, preferably 1-5% by weight.

Alternatively, a polymer may be used which incorporates the alkyl phosphoric acid directly into a side chain of the polymer. For example, any acid insensitive polymer that has a hydroxyl group on the side chain may be reacted with a phosphoric acid to produce an alkyl or aromatic phosphoric acid polymeric derivative, which then may be used as is or partially neutralized with a Group I metal, Group II metal or transition metal to form a biocidal composition.

Group I metal ions which may be used according to the present invention include H, Li, Na, K, Rb, Cs, Cu, Ag and Au. Group II metal ions, which may be used according to the present invention includes Be, Mg, Ca, Sr, Ba, Zn, Cd and Hg. Transition metal ions suitable in the present invention include Sc, Ti, V, Cr, Mn, Fe, Co, Ni, Y, Zr, Nb, Mo, Tc, Ru, Rh, Rd, Pd, La, Hf, Ta, W, Re, Os, Ir, Pt.

The polymers may be mixed with nonpolymeric "extenders" or "fillers", for example, clay, $CaCO_3$, diatomatious earth, alumina trihydrate, barium sulphate, talc, calcium silicate, and magnesium silicate, in a range of 0.5% to 10.0% by weight.

As described in copending application U.S. Ser. No. 190,370, filed May 5, 1988 by Robert McIntosh, entitled "Biocidal Delivery System and Method of Preparation Thereof", incorporated herein by reference, carrier materials such as diatomaceous earth or other high-surface area particulate inert materials actually extend the period of time during which the biocidal material is active against organisms. The substituted alkyl phosphoric acid is adsorbed onto the material, and is slowly released over time. Other materials which may be used include cationic synthetic resins and natural polymers, for instance, chitin, gelatin, and collagen, having quaternary amine sites or free amine functions, and polymeric microcapsules.

A mono-alkyl phosphoric acid may be produced by reacting $P_2O_5$ with an alcohol, or by any other method known to those skilled in the art. Alternatively, one may buy the mono-alkyl phosphoric acid commercially.

One mole of $P_2O_5$ reacted with three moles of alcohol produces a mixture of mono-alkyl phosphoric acid along with some di-alkyl phosphoric acid. The di-alkyl phosphoric acid is a stronger acid than the mono-alkyl phosphoric acid, and therefore, preferentially reacts with a base added to the product mixture to form a salt. For example, 1.0 m of mono-alkyl phosphoric acid and 1.0 m of di-alkyl phosphoric acid reacted with 1.3 m of an amine produces approximately 1.0 m of ammonium di-alkyl phosphate, 0.3 m of ammonium mono-alkyl hydrogen phosphate and 0.7 m of mono-alkyl phosphoric acid.

In the preferred embodiment, the mono-alkyl phosphoric acid is partially neutralized with an organic substituted amine to produce an ammonium salt of an alkyl phosphoric acid.

The alkyl phosphoric acid may instead be partially neutralized with a Group I metal, Group II metal, or transition metal. For example, the alkyl phosphoric acid may be partially neutralized with sodium hydroxide or potassium hydroxide, to produce the sodium or potassium salt of the alkyl phosphoric acid, respectively. Alternatively, the alkyl phosphoric acid may be partially neutralized with magnesium acetate or zinc acetate, to produce the corresponding salts. Since magnesium and zinc are in a +2 oxidation state, each zinc or magnesium ion will coordinate with two molecules of alkyl phosphoric acid.

Selection of the positive ion affects biocidal activity, principally the anti-Gram-negative bactericidal activity, although the alkyl phosphoric acid appears to be the primary source of biocidal activity. The biocidal activity is also a function of the relative ratio of mono- to di-alkyl substituted phosphoric acid ester.

The polymeric composition may also include a surfactant to improve the properties of the composition.

The polymeric coating is applied by dipping, brushing or spraying the coils. The coils are then dried with or without heat.

Without further elaboration, it is believed that one skilled in the art can, using the preceding description, utilize the present invention to the fullest extent. The following specific embodiments, are, therefore, to be construed as merely illustrative, and not limiting of the remainder of the disclosure. Percentage of composition is by weight unless otherwise indicated.

EXAMPLE 1

To 1 m of $P_2O_5$ is slowly added 3 m of 2-ethylhexanol with vigorous stirring at a reaction temperature of 100° C. The reaction is complete in about two hours. The progress of reaction is monitored by titrating the acid produced with a solution of base. The reaction products include mono-(2-ethylhexyl)phosphoric acid and di-(2-ethylhexyl)phosphoric acid.

The antimicrobiocidal activity is tested by plating a microorganism onto trypticase soy nutrient agar, or other appropriate media, punching 6 mm diameter, 5 mm deep holes into the agar, and applying 0.05 ml of each of the undiluted test compounds into the holes. The petri-dish is examined for growth of the microorganisms after incubation for 24 hours at 30° C. The diameter of the clear area surrounding the hole containing the compound being tested is indicative of the degree of antimicrobiocidal activity.

EXAMPLE 2

To form the ammonium salt of the alkyl phosphoric acid mixture, the products from Example 1 may be reacted with an amine, such as bis-(2-hydroxyethyl)-cocoamine. For example, 1.3 m of bis-(hydroxyethyl)-cocoamine is slowly added to 2.0 m of the reaction products of Example I (assuming an equal product mixtures of mono- and di-alkyl phosphoric acid) until the pH is between approximately 2 and 5 in a 75% ethanol water solution. The reaction may be carried out in a temperature range from approximately 60° C. to 120° C. until the reaction is complete.

EXAMPLE 3

The zinc salt of the alkyl phosphoric acid mixture may be prepared by mixing 53 g of 2-ethylhexyl phosphoric acid with 15 g of zinc acetate ($Zn(OCO_2CH_3)_2.2H_2O$). These reagents are mixed and the acetic acid is removed by vacuum distillation.

EXAMPLE 4

The magnesium salt of the alkyl phosphoric acid mixture may be prepared by reacting 20 g of magnesium acetate ($Mg(OCO_2CH_3)_2.4H_2O$) with 53 g 2-ethylhexyl phosphoric acid. The reagents are mixed and warmed, and the acetic acid is stripped off by vacuum distillation.

EXAMPLE 5

The magnesium phosphate and zinc phosphate compounds were washed and evaluated for biocidal activity using the standard cut method test procedure:

A sterile nutrient ager solution was prepared. The nutrient ager was innoculated with a 24 hour culture of either *Staphylococcus aureus* (Gram-positive) or *Pseudo-*

*monas aeroginosa* (Gram-negative) organisms. The inoculated ager was poured into a 100×15 mm sterile petri-dish and allowed to solidify at room temperature. After solidifying small reservoirs were punched for the compounds to be tested. Magnesium phosphate was added to one well and zinc phosphate added to another. The plates were then incubated 24 hours at 30° C. and examined for zones of inhibition. The zone of inhibition of Staphylococcous was 15 mm for the magnesium phosphate and 19 mm for the zinc phosphate. No inhibition of the Pseudomonas was observed, however, the results clearly demonstrate the Group II and transition metal salts of alkyl phosphoric acids have bactericidal activity.

The alkyl phosphoric acid of the above described composition may be mixed with the polymer in a ratio of 0.25 to 10% alkyl phosphoric acid to 99.75% to 90% polymer. In addition, a non-ionic surfactant, for example, ethoxylated nonylphenol, may be added in an amount up to 2.5%. Furthermore, fillers and extenders may be added to this polymeric composition.

EXAMPLE 6

A biocidal protective coating for heat exchangers may be prepared by mixing a ratio of 95% fluoropolymer dispersion, such as Teflon® NPA soil and stain repellent, which contains 0 to 5% polyfunctional perfluoral alkyl ester and 1 to 10% perfluoroalkylmethylacrylate copolymers, with 2.5% of the partially neutralized alkyl phosphoric prepared in accordance with Example 2, and 2.5% ethoxylated nonylphenol.

EXAMPLE 7

Alternatively, a biocidal protective coating for heat exchanger coils may have a composition of 47.5% aqueous Teflon® NPA soil and stain repellent fluorochemical dispersion, 47.5% polyethylene emulsion, 2.5% of a partially neutralized alkyl phosphoric acid made in accordance with Example 2, and 2.5% ethoxylated nonylphenol (surfactant). For example, the surfactant may be mixed with the product of Example II, and this mixture added to the Teflon® dispersion. The polyethylene emulsion is then added to the Teflon® mixture. This composition is then ready for use as a coating.

EXAMPLE 8

A biocidal protective coating for heat exchanger coils may be prepared from 47.5% Teflon® NPA soil and stain repellent aqueous fluorochemical dispersion, 47.5% ethylene vinyl acetate emulsion, 2.5% of partially neutralized alkyl phosphoric acid made in accordance with Example 2, and 2.5% ethoxylated nonylphenol.

This coating may be applied to any type of metal coil, including those made from copper, iron, brass, or aluminum, or metal alloy which contains zinc, manganese, silicon, chromium, nickel, magnesium or carbon.

The coils may be coated with this polymeric composition by dipping the coil into a dispersion of the polymeric composition, spraying the materials onto the coils, or brushing the materials onto the coils. The coils may be coated to any desirable thickness, preferably 2-5 mils (1 mil=3/1000 inch).

EXAMPLE 9

Coils may be dipped into a dispersion containing a perfluorinated polymer in a ratio of 0.25-10% by weight to the partially neutralized alkyl phosphoric acid produced as in Example 2, dried at a temperature range from 50° C. to 150° C. for a time period from seconds to 10 min. The coils may be coated with the polymeric composition to a thickness of from 0.5 mils to 5.0 mils.

EXAMPLE 10

Coils were dipped into a dispersion containing 98% fluorocarbon, 2% of partially neutralized alkyl phosphoric acid made in accordance with Example 2, and dried at 180° F. for ten minutes. The coils were coated with three ounces of the mixture.

EXAMPLE 11

Coils are sprayed with a dispersion containing 98% fluorocarbon, 2% of partially neutralized alkyl phosphoric acid made in accordance with Example 2, and dried at 180° F. for ten minutes. The coils are coated with three ounces of the mixture.

EXAMPLE 12

Coils are brushed with a dispersion containing 98% fluorocarbon, 2% of partially neutralized alkyl phosphoric acid made in accordance with Example 2, and dried at 180° F. for ten minutes. The coils are coated with three ounces of the mixture.

EXAMPLE 13

The coating made in accordance with Example 10 was dried and the coils were run in the cooling mode for 700 hours (approximately equal to three years of actual use of an automobile air conditioner), along with a non-treated coil. After 700 hours, the coated coils showed no signs of corrosion due to exposure to water or other airborne chemicals. A visual comparison of the coated coils and uncoated coils established that the coated coils had accumulated less particular matter, indicative of less "fouling" on the coils.

EXAMPLE 14

A coil prepared in accordance with Example 10, along with an uncoated coil, were subjected to a fine mist of salt spray (sodium chloride) for 21 days and a visual comparison made. The coil coated with Teflon® NPA soil and stain repellent and partially neutralized alkyl phosphoric acid showed no signs of corrosion due to pitting from salty water. Visual observation established that the coated coil had accumulated less particulate ( matter than the uncoated coil.

EXAMPLE 15

Four sets of coils were prepared separately with 98% polyacrylate and 2% of the partially neutralized alkyl phosphoric acid from Example 2; 98% polyethylene and 2% of partially neutralized phosphoric acid from Example 2; 97.5% polyvinyl acetate and 2.5% of the partially neutralized alkyl phosphoric acid from Example 2; and 95% Teflon® NPA soil and stain repellent with 5% of the partially neutralized alkyl phosphoric acid from Example 2. These coils were inoculated with *Aspergillus niger, Aspergillus flavus* and *Penicillin funiculogum.* An uncoated coil was likewise innoculated. These coils were run in the cooling mode continuously for 21 days, and then visually observed for fungal growth. As seen in Table I, the uncoated coil showed a heavy growth of fungi after 14 days. The polyacrylate and polyethylene coatings showed only little growth of fungi after 21 days, while the polyvinylacetate showed only moderate growth of fungi after 21 days. Superior resistance to fungal growth was shown by the fluorocarbon in combination with 5% of the partially neutralized alkyl phosphoric acid, in that there was no fungal growth after 21 days.

TABLE I

Resistance to Fungal Growth

| Type Coating | Percentage Partially Neutralized Alkyl Phosphoric Acid from Example II | 7 Days | 14 Days | 21 Days |
|---|---|---|---|---|
| None | 0 | 3 | 3–4 | 4 |
| Acrylate | 2 | 1 | 2 | 2 |
| Polyethylene | 2 | 1–2 | 1–2 | 1–2 |
| Polyvinylacetate | 2.5 | 2 | 3 | 3 |
| Teflon ® | 5 | 0 | 0 | 0 |

0 = No Growth (Excellent Resistance)
1 = Trace of Growth (Very Good Resistance)
2 = Little Growth (Good Resistance)
3 = Moderate Growth (Poor Resistance)
4 = Heavy Growth (No Resistance)

EXAMPLE 16

Aluminum plates were coated with a composition of 95% Teflon ® NPA soil and Stain Repellant, 2.5% of the product of Example 2, and 2.5% exothylated nonylphenol. A thin layer of dilute nutrient agar was poured onto the plate, and the agar was innoculated with both *Staphylococcus aureus* and *Pseudomonas aeroginosa*. The plates were incubated for up to 72 hours. No bacterial growth was observed at the agar/coating interface.

EXAMPLE 17

An electron microscope X-ray analysis was made on the coating of Example 10 before and after seven hundred hours of use. The X-ray analysis indicated that approximately 50% of the phosphorus remained in the polymeric composition after this time.

This invention has been described with reference to its preferred embodiments. Variations and modifications of the coating for, and method of coating heat exchanging metal coils will be obvious to those skilled in the art from the foregoing detailed description of the invention. It is intended that all these variations and modifications be included within the scope of the appended claims.

We claim:

1. A coating for heat exchangers, comprising:
   (a) a water resistant organic polymeric material, wherein the material bonds to the surface of a heat exchanger; and
   (b) a biocidally effective amount of a substituted phosphoric acid of the general formula

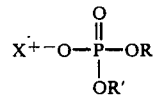

wherein X is selected from the group consisting of organic ions, H+Group I metals, Group II metals and transition metals, R and R' are selected from the group consisting of hydrocarbons and substituted hydrocarbons having not more than 24 carbon atoms, one of R or R¹, can be H, and there is at least one free hydroxyl group.

2. The coating of claim 1 wherein X+ is an ammonium ion.

3. The coating of claim 1 wherein X+ has the general formula

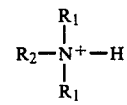

wherein $R_1$ is selected from the group consisting of $C_1$ to $C_{18}$ hydrocarbons and a hydroxy alkyl group of from 2 to 18 carbon atoms; and $R_2$ is an alkyl group of from 8 to 18 carbons.

4. The coating of claim 1 wherein X+ is bis-(2-hydroxyethyl)-cocoamine.

5. The coating of claim 1 wherein R and R' are selected from the grouping consisting of H and 2-ethylhexyl.

6. The coating of claim 1 wherein the polymeric material comprises a polymer or copolymer made from an alkene, diene, vinyl ester, acrylic acid, methacrylic acid, alkyl methacrylate, vinyl halide, styrene, or vinylidene halide or mixtures thereof, and at least some of the hydrogens of these monomers may be replaced with fluorine.

7. The coating of claim 6 wherein the polymeric material is perfluorinated.

8. The coating of claim 6 wherein the polymeric material comprises a polyfunctional perfluoroalkyl ester.

9. The coating of claim 6 wherein the polymeric material comprises a perfluoroalkyl methacrylate polymer or copolymer.

10. The coating of claim 6 wherein the polymeric material comprises Teflon ® NPA soil and stain repellant.

11. The coating of claim 1 wherein the substituted phosphoric acid is incorporated into the side chain of the polymer.

12. The coating of claim 1 which contains a non-ionic surfactant.

13. The coating of claim 1 further comprising non-polymeric extenders.

14. The coating of claim 13 wherein the nonpolymeric extenders are selected from the group consisting of clay, calcium carbonate, diatomatous earth, alumina trihydrate, barium sulphate, talc, calcium silicate, and magnesium silicate.

15. The coating of claim 14 wherein the nonpolymeric extenders are added in a range of 0.5% to 10.0% by weight.

16. A method of coating a heat exchanger coil comprising:
   (a) Applying a polymeric composition which comprises a water resistant organic polymer and a biocidally effective amount of a substituted phosphoric acid of the general formula

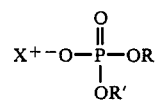

wherein X is selected from the group consisting of organic ions, H+, Group I metals, Group II metals, transition metals, R and R' are independently selected from the group consisting of hydrocarbons and substituted hydrocarbons having not more than 24 carbon atoms, and there is at least one free hydroxyl group.

17. The method of claim 16 wherein $X^+$ is an ammonium ion.

18. The method of claim 16 wherein $X^+$ has the general formula

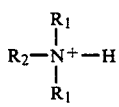

wherein $R_1$ is selected from the group consisting of $C_1$ to $C_{18}$ hydrocarbons and a hydroxy alkyl group of from 2 to 18 carbon atoms; and $R_2$ is an alkyl group of from 8 to 18 carbons.

19. The method of claim 16 wherein $X^+$ is bis-(2-hydroxyethyl)-cocoamine.

20. The method of claim 16 wherein R and R' are selected from the grouping consisting of H and 2-ethylhexyl.

21. The method of claim 16 wherein the polymeric material comprises a polymer or copolymer made from an alkene, diene, vinyl ester, acrylic acid, methacrylic acid, vinyl halide, styrene, or vinylidene halide or mixtures thereof, and at least some of the hydrogens of these monomers may be replaced with fluorine.

22. The method of claim 21 wherein the polymeric material is perfluorinated.

23. The method of claim 21 wherein the polymeric material comprises a polyfunctional perfluoroalkyl ester.

24. The method of claim 21 wherein the polymeric material comprises a perfluoroalkyl methacrylate polymer or copolymer.

25. The method of claim 21 wherein the polymeric material comprises Teflon ® NPA soil and stain repellant.

26. The method of claim 16 wherein the substituted phosphoric acid is incorporated into the side chain of the polymer.

27. The method of claim 16 further comprising providing a non-ionic surfactant with the polymeric composition.

28. The method of claim 16 further comprising providing nonpolymeric extenders with polymeric composition.

29. The method of claim 28 wherein the nonpolymeric extenders are selected from the group consisting of clay, calcium carbonate, diatomatous earth, alumina trihydrate, barium sulphate, talc, calcium silicate, and magnesium silicate.

30. The method of claim 28 wherein the nonpolymeric extenders are added in a range of 0.5% to 10.0% by weight.

31. The method of claim 16 wherein the polymeric composition is applied by dipping the coil into a dispersion of the coating.

32. The method of claim 16 wherein the polymeric composition is applied by spraying the coil.

33. The method of claim 16 wherein the polymeric composition is applied by brushing the coating onto the coil.

* * * * *